(12) United States Patent
Afornali

(10) Patent No.: US 11,883,453 B2
(45) Date of Patent: Jan. 30, 2024

(54) FORMULATION BASED ON MEDICINAL PLANT, OR PART OR EXTRACT THEREOF, USE OF THE FORMULATION AND PRODUCT INCLUDING SAID FORMULATION

(71) Applicant: PHYTOPLENUS BIOATIVOS S.A., Pinhais (BR)

(72) Inventor: Alessandro Afornali, Curitiba (BR)

( * ) Notice: Subject to any disclaimer, the term of this patent is extended or adjusted under 35 U.S.C. 154(b) by 224 days.

(21) Appl. No.: 17/288,578

(22) PCT Filed: Oct. 29, 2019

(86) PCT No.: PCT/BR2019/050468
§ 371 (c)(1),
(2) Date: Apr. 26, 2021

(87) PCT Pub. No.: WO2020/087146
PCT Pub. Date: May 7, 2020

(65) Prior Publication Data
US 2021/0353699 A1    Nov. 18, 2021

(30) Foreign Application Priority Data
Oct. 29, 2018    (BR) .......................... 102018072258-1

(51) Int. Cl.
| | | |
|---|---|---|
| *A61K 36/28* | (2006.01) |
| *A61P 17/02* | (2006.01) |
| *A61K 47/02* | (2006.01) |
| *A61K 47/10* | (2017.01) |
| *A61K 47/14* | (2017.01) |
| *A61K 47/18* | (2017.01) |
| *A61K 47/22* | (2006.01) |

(52) U.S. Cl.
CPC .............. *A61K 36/28* (2013.01); *A61K 47/02* (2013.01); *A61K 47/10* (2013.01); *A61K 47/14* (2013.01); *A61K 47/18* (2013.01); *A61K 47/186* (2013.01); *A61K 47/22* (2013.01); *A61P 17/02* (2018.01)

(58) Field of Classification Search
None
See application file for complete search history.

(56) References Cited

U.S. PATENT DOCUMENTS

2013/0287708 A1* 10/2013 Silberstein ........... A61K 8/9794
514/25
2014/0349902 A1* 11/2014 Allef ...................... A61Q 19/10
510/491

FOREIGN PATENT DOCUMENTS

| CN | 107625667 A | 1/2018 |
| EP | 3192519 A2 | 7/2017 |
| WO | 2018145966 A1 | 8/2018 |

OTHER PUBLICATIONS

Costa et al. (BR102015025680A2 Google Machine Translation) (Year: 2015).*
Ghosh, P.K. & Gaba, A. Phyto-extracts in wound healing. J Pharm Pharm Sci. 2013. vol. 16, No. 5, pp. 760-820 doi: 10.18433/j383v.
Randhawa, K.K.S. & Rahman, P.K.S.M. Rhamnolipid biosurfaces-past, present and future scenario of global market. Front. Microbiol. 2014 vol. 5: 454 dol 10.3389/fmich.2014 .00454.
Buzzi, M et al. Pressure ulcer healing with Plenusdermax (R) Calendula officinalis L. Extract. Rev Bas Enferm 2016 vol. 69, No. 2, pp. 250-257 doi: 10.1590/0034-7167.2016690297.

* cited by examiner

*Primary Examiner* — Robert A Wax
*Assistant Examiner* — Quanglong N Truong

(57) ABSTRACT

This invention refers to a formulation comprising at least one medicinal plant, part or extract of it, one or more extracting agents and one or more pharmaceutically or cosmetically acceptable excipients that generate a plant extract (plant derivative) with a high bioactive content for regeneration of the skin, dermal mucous membrane and related parts, used as an active pharmaceutical ingredient to treat wounds of any kind or as a cosmetic ingredient for protection, maintenance and natural balance of the skin, dermal mucous membrane and related parts.

The use of this formulation generates pharmaceutical products of high efficacy, of topic used, which provide treatments of low cost, reduced time and of less complexity of the procedures by the healthcare professionals, intended to the treatment of chronic and acute lesions of the skin, dermal mucous membrane and related parts.

The use of this formulation still generates cosmetic products, of topic use, aiming at the protection, maintenance and natural balance of the skin, dermal mucous membrane and related parts.

20 Claims, 9 Drawing Sheets

FORMULATION BASED ON MEDICINAL PLANT, OR PART OR EXTRACT THEREOF, USE OF THE FORMULATION AND PRODUCT INCLUDING SAID FORMULATION

INVENTION FIELD

This invention refers to a formulation comprising at least one medicinal plant, part or extract of it, one or more extracting agents and one or more pharmaceutically or cosmetically acceptable excipients that generate a plant extract (plant derivative) with a high bioactive content for regeneration of the skin, dermal mucous membrane and related parts, used as an active pharmaceutical ingredient to treat wounds of any kind or as a cosmetic ingredient for protection, maintenance and natural balance of the skin, dermal mucous membrane and related parts.

The use of this formulation generates pharmaceutical products of high efficacy, of topic used, which provide treatments of low cost, reduced time and of less complexity of the procedures by the healthcare professionals, intended to the treatment of chronic and acute lesions of the skin, dermal mucous membrane and related parts.

The use of this formulation still generates cosmetic products, of topic use, aiming at the protection, maintenance and natural balance of the skin, dermal mucous membrane and related parts.

BACKGROUND OF THE INVENTION

It is estimated that the entire world population, approximately 7.4 billion people, does at least one acute injury per year and around 2% of the global population (according to WHO), causes chronic injuries, equivalent to about 149 million people, higher than the population of Russia, with 142 million people.

The worldwide incidence of these injuries can be divided by origin type of the injuries. According to data from 2013, most injuries were due to surgery (102.8 million) and, subsequently, to lacerations (21.4 million). Ulcers were responsible for 29.7 million injuries: 11.3 million were due to diabetic ulcers, 11 million due to venous ulcers and 7.4 million due to pressure injuries. Another 9.8 million injuries were due to burns and 1 million injuries due to various reasons.

The injuries occur as a result of an extensive variety of trauma, from simple cuts to extreme injuries, which result in a rupture of the anatomical structure of the skin, with the subsequent loss of its protective function, among other purposes.

Injuries are classified into:
Acute Injuries: They are characterized by the ability of the metabolism itself to promote healing through a normal physiological process, with cicatrization occurring in about 21 days. Examples of acute injuries include cuts, abrasions, surgical incisions and partial-thickness burns.
Chronic Injuries: Characterized by a prolonged inflammatory reaction that interferes with the normal cicatrization process, among other parameters, which require medical supervision and specific medications or devices. This type of injury is also characterized when healing does not occur within 42 days, among other criteria. Examples of this type of injury are diabetic foot ulcers, venous ulcers, pressure injuries, arterial ulcers, infected surgical incisions and full-thickness burns.

Cicatrization is a tissue repair process that replaces the injured tissue with new tissue. It is a dynamic process that involves biochemical and physiological phenomena that occur in a coordinated and harmonious way in order to guarantee tissue restoration. It is formed by three overlapping evolutionary phases: initial or inflammatory phase, proliferative or fibroplasia phase and remodeling or maturation phase.

Several factors can influence cicatrization, including: type of lesion, age of the patient, nutritional status, anatomical location, skin type, race, surgical technique used, existence of chronic diseases, smoking, infection, use of drug therapy and appropriate topic treatment.

Therapies for treatment of injuries may use products in the following categories:
Traditional: as, for example, dry dressings, adhesives and bandages that have the function of protecting and covering the lesion;
Advanced: like, for example, hydrocolloids, hydrogels and alginates. These are products that, in addition to the traditional products category, promote a moist environment in the lesion bed, favoring cicatrization conditions;
Active: like products based on active agents, called synthetic skins, products that are temporary skin substitutes and products that are permanent skin substitutes (grafts). These are products that, in addition to the performance of the advanced products category, stimulate the cicatrization process; and
Medical Devices: Therapies that use devices that aim to improve the cicatrization process through different technologies. As examples, we have: hyperbaric chamber, Vacuum Assisted Closure (VAC) devices and ultrasound devices, among others.

The pharmaceutical industries are focused and continue to invest in products that use diverse and expensive technologies to generate physical membranes based on living tissues or synthetic fabrics, in the category of Active products, which require treatments that incur:
High cost of treatment: As an example, a single Apligraf® dressing, recognized as one of the most effective on the market, has a cost of $34.47 per $cm^2$, with an estimate of replacement up to every 7 days. In addition to this cost, there are also expenses related to:
a) Professionals: healthcare professionals needed for the implantation of these dressings and periodic assistance for the treatment of these patients, in addition to surgical centers or proper areas for carrying out medical and nursing procedures;
b) Need for drugs and additional materials associated with the treatment; and
c) Quantity of these dressings needed to cover the entire length of the chronic injury, usually of expressive area, throughout the treatment.
Extended treatment time: The treatment time with a product of this nature is usually long lasting, either due to the complexity required in the treatment of the injury, or due to the therapeutic effect of the product itself.
Complex treatment procedures: the solid presentation of these products are physical membranes that cause several inconveniences to patients and healthcare professionals due to the following conditions:

a) Because they completely cover the injury surface, the membranes cannot be applied, indiscriminately, without prior medical evaluation;

b) Once the use is approved, the application of these products always requires the assistance of healthcare professionals, in addition to a technically appropriate physical environment;

c) In the hypothesis of infection, a common situation in chronic injuries, the beginning of the application of the membranes can only occur after the previous treatment of this infection in the injury;

d) Membranes can present cases of adverse reactions due to the existence of allergenic elements;

e) Some membranes can significantly increase the secretion of the injury, affecting the skin at the extremities of the injury, generating inappropriate cicatrization; and f) There is discomfort caused by physical contact of the membrane with the injured region, an area of high sensitivity to pain, in general.

The emergence of the Active and Medical Device product categories was a natural consequence of the low perceived effectiveness of Traditional and Advanced products in the treatment of chronic injuries.

One of the products on the market for the treatment of injuries is Plenusdermax®. An active pharmaceutical ingredient, produced by process technology, for compounding of a healing herbal medicine, based on *Calendula officinalis* L. and excipients (Butylated Hydroxytoluene—BHT, ethanol, polyethylene glycol, phenoxyethanol, caprylyl glycol, sodium bicarbonate and purified water). The extract is used for compounded topical preparations to treat lesions of the skin and mucous membrane, promoting healing and combating possible inflammatory spots.

In any case, remains a need in the market to seek a more effective product that provides low-cost treatment, with a reduced treatment time and with minimal complexity in procedures by healthcare professionals.

Objective of the Invention

A first objective is to provide a formulation comprising at least one medicinal plant, part or extract of it, one or more extracting agents and one or more pharmaceutically or cosmetically acceptable excipients that generate a plant extract (plant derivative) with a high content of bioactive for regeneration of the skin, dermal mucous membrane and related parts, where the formulation has a pH in the range of 4.5 to 10 and at least one extracting agent is a biosurfactant. This formulation is intended for topic use to treat injuries of any nature on the skin, mucous membrane and related parts in the pharmaceutical field and to protect, maintain and balance the natural regeneration of the skin, mucous membrane and related parts in the cosmetic context.

A second objective is to provide the use of the mentioned formulation, resulting in drugs that provide medical treatments, as well as products for cosmetic applications, both of which are low cost, reduced time and minimal complexity of healthcare professional procedures and in the cosmetology sector, respectively.

A third objective is the description of a product comprising the said formulation for use on the skin, dermal mucous membrane and related parts, whether in the pharmaceutical field in the treatment of chronic and acute injuries, as well as in the cosmetic context for protection, maintenance and balance of natural regeneration of the skin, dermal mucous membrane and related parts.

BRIEF DESCRIPTION OF THE INVENTION

The first objective is achieved by providing a formulation comprising at least one medicinal plant, part or extract of it, one or more extracting agents and one or more pharmaceutically or cosmetically acceptable excipients, where the formulation has a pH in the range of 4.5 to 10, and in which at least one extracting agent is a biosurfactant. Said excipients can be selected from antioxidants, preservatives, precipitants, solvents and pH modulators (alkalizing or acidulating). Said formulation can be used as an Active Pharmaceutical Ingredient (API) or as a cosmetic ingredient.

The second objective is achieved by using this formulation, as Active Pharmaceutical Ingredient (API), in the composition of medicines for the regeneration of the skin, dermal mucous membrane and related parts or as an ingredient in the composition of cosmetics for the maintenance and natural balance of the skin, dermal mucous membrane and related parts, both topically applied.

The third objective is achieved by being able to obtain a finished pharmaceutical product, which can be industrialized or compounded, using said formulation, protection, maintenance and balance of the natural regeneration of the skin, dermal mucous membrane and related parts, in the cosmetic scope, or to accelerate tissue regeneration of the skin, dermal mucous membrane and related parts, in the pharmaceutical field.

In an alternative embodiment, the third objective is achieved by being able to obtain a finished cosmetic product using said formulation to protect, maintain and guarantee the balance of the natural regeneration of the skin, dermal mucous membrane and related parts. The product is of topic use, as, for example, in the form of presentation of an after-sun lotion, and may have other cosmetic applications and other forms of presentation, such as, for example, gels, creams and ointments.

DETAILED DESCRIPTION OF THE INVENTION

Figure 1:
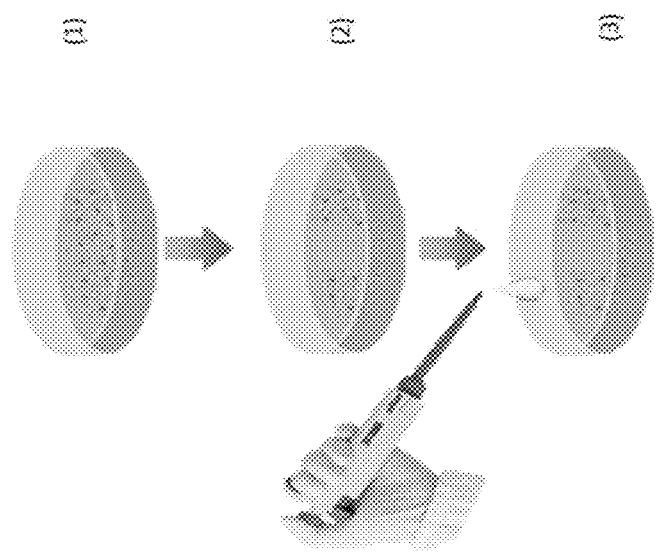
FIG. 1—Flow chart of the execution of the in vitro cell migration test used. (1). Plate replication of human fibroblasts (HFF1) (2). After 24 hours, the scratching and image capture (3) are performed. Incubation with treatments (0.02%).

For reference purposes, nails, hair, sebaceous glands and sweat glands are considered to be related to the skin and dermal mucous membrane.

Yet, unless specifically disclosed on the contrary, "at least one" is understood to mean the presence of one, two, three, four, five, six or more elements defined in the present invention.

The formulation described here is obtained from a medicinal plant, part or extract of it, many of which are traditionally known to act on the treatment of skin lesions, in combination with one or more extracting agents and one or more pharmaceutically or cosmetically acceptable excipients, in which the formulation has a pH in the range of 4.5 to 10, and in which at least one extracting agent is a biosurfactant, which helps in the extraction process, generating a plant extract (vegetable derivative) with a high content of similar bioactive not found on the market, capable of accelerating the treatment of injuries, chronic or acute, and may be less than half the treatment time, when compared to other products and methods currently used.

This technology encompasses a single product, through the combination of specific ingredients and an optimized and standardized extraction method, which expressively extract specific bioactive agents, mainly triterpenoid monoesters, important for healing action, resulting in a product with potential for modulation of several biological mechanisms in the lesion bed and that provide high efficacy for the patient's healing, including antimicrobial, anti-inflammatory action, tissue repair, cell proliferation and migration, restructuring of the extracellular and curative matrix by means of a biomolecular film formed by the product. Due to this performance of specific natural bioactive agents, in the healing field of the skin, as well as the superior treatment efficiency compared to other conventional drugs used for the regeneration of chronic and acute injuries, it can be assured that there is a unique product in the global market. The following bioactive triterpenoid monoesters comprise: lupeol, calenduladiol laurate, arnidiol laurate, faradiol laurate, calenduladiol myristate, arnidiol myristate, faradiol myristate, calenduladiol palmitate, arnidiol palmitate and faradiol palmitate.

The choice of enrichment of triterpenoid monoesters, in the present formulation, was adopted with the objective of obtaining a product with high efficacy in skin healing mechanisms. The scientific basis for the beneficial properties of triterpenoid monoesters and their potential action as a healing agent are supported by several scientific researches.

In 2015, Agra and collaborators published a review to address this issue exclusively and used systematic searches of original works published from 1910 to 2013 in the Medline, ScienceDirect and LILACS databases. The conclusion, based on the analysis of more than two thousand articles that were researched, is that triterpenoids induced a reduction in the time to close the lesions in practically all types of injuries.

Based on the reported mechanisms of action, triterpenoids also modulate the production of ROS free radicals in the lesion microenvironment, accelerating the tissue repair process, inducing cell migration, cell proliferation and collagen deposition at the injured site (Agra, et al. 2015).

Patel et al., in another study published in 2018, evaluated the biological potential of antioxidant activity and microbial agent. The paper concluded that Lupeol, effectively, has excellent properties to eliminate free radicals at a rate proportional to the concentration of the triterpenoid monoesters used. The tests performed, using the disk-diffusion methodology, confirmed the antimicrobial activity by observing the inhibition halos in the formed agar.

In parallel, cytotoxicity tests were performed, using the MTT method with 3T3 fibroblast strains for Lupeol, and the data identified acceptable viability and no toxicity found. Based on this study, it was possible to conclude that the triterpenoids present in the extract of Calendula have a proven role of antioxidant and antimicrobial action without any indication of cytotoxicity (Pavel et al., 2018).

Some papers show the role of another monoester very abundant in the extracts of Calendula, faradiol. This component has an antiinflammatory role and promotes acceleration of the healing process when topically applied. Della Loggia and colleagues studied ways to increase the amounts of this triterpenoid monoester in the extracts, and the results of the anti-inflammatory action are proportional to the concentrations obtained of faradiol in the extract, concluding its role in the mechanism of injury repair (Della Loggia et al., 1994).

In 2009, Fronza and colleagues conducted studies with Calendula extract and triterpenoid monoesters, such as palmitate and faradiol myristate, to determine the effect of in vitro healing using the Scratch Assay technique on 3T3 fibroblast strains. It was observed that faradiol, in the forms of myristate and palmitate, has a partial role in the healing process compared to the extract, so it is possible to infer that faradiol is one of the triterpenoid components that also act in cicatrization, however it is the set of all these monoesters triterpenoids that synergistically enhances the tissue repair mechanism as a whole (Fronza et al., 2009).

This formulation, rich in bioactive and high levels of triterpenoid monoesters, has at least one medicinal plant, part or extract of it used for the regeneration of skin, dermal mucous membrane and related parts.

In a preferred modality, medicinal plants (herbal drugs) that can be used to produce plant extracts are sources of obtaining triterpenoid monoesters. In addition to the aforementioned *Calendula officinalis*, said medicinal plants are preferably selected from, without limitation to: *Acacia senegal, Achillea millefolium, Aesculus hippocastanum, Agrimonia eupatoria, Ajuga turkestanica, Alcea rosea, Alchemilla vulgaris, Aleurites moluccana, Aloe barbadensis, Aloe vera, Althaea officinalis, Ammi visnaga, Ananas sativus, Anethum graveolens, Angelica archangelica, Anthemis nobilis, Arachis hypogaea, Arctium lappa, Arctostaphylos* sp., *Argania spinosa, Arnica montana, Artemisia absinthium, Artemisia capillaris, Artemisia vulgaris, Ascophyllum nodosum, Astragalus membranaceus, Astragalus sinicus, Atractylodes lancea, Avena* sp., *Bellis perennis, Berberis aristata, Berberis vulgaris, Bertholletia excelsa, Beta vulgaris, Betula alba, Boerhavia difusa, Borago officinalis, Boswellia carterii, Brassica campestres, Brassica oleracea, Brassica rapa, Buddleja davidii, Bupleurum falcaturn, Butyrospermurn parkii, Buxus chinensis, Calendula arvensis, Calendula bicolor, Calendula eckerleinii, Calendula/anzae, Calendula maderensis, Calendula maritima, Calendula maroccana, Calendula meuselii, Calendula persica, Calendula stellata, Calendula suffruticosa, Calendula tripterocarpa, Calluna vulgaris, Calophyllum inophyllum, Camellia japonica, Camellia oleifera, Camellia sinensis, Cannabis sativa, Carthamus tinctorius, Carya iffinoensis, Castanea sativa, Cedrus atlantica, Centaurea cyanus, Centella asiatica, Chamaemelum nobile, Chamomilla recutita, Chondrus crispus, Citrullus colocynthis, Citrus aurantifolia, Citrus aurantium, Citrus medica, Citrus unshiu, Coffea arabica, Cola acuminata, Coleus barbatus, Commiphora myrrha, Copaifera officinalis, Copernicia cerifera, Cornus* sp., *Corylus americana, Corylus avellana, Crataegus monogyna, Cucumis melo, Cucumis sativus, Cucurbita pepo, Curcuma longa, Cymbopogon citratus, Cymbopogon martini, Diplolepis rosae, Echinacea purpurea, Elaeis guineenses, Epilobium* sp., *Equisetum arvense, Eriobotrya japonica, Eucalyptus* sp., *Eugenia aromatica, Eugenia caryophyllus, Euphorbia cerifera, Euphrasia officinalis, Euterpe oleracea, Evodia rutaecarpa, Fagus sylvatica, Filipendula glaberrima, Filipendula rubra, Filipendula ulmaria, Fucus vesiculosus, Gardenia jasminoides, Gentiana lutea, Geranium pratense, Ginkgo biloba, Glyzyrrhiza glabra, Gossypium herbaceum, Hamamelis* sp., *Hapagophytum procumbens, Helianthus annuus, Hibiscus* sp., *Hippophae rhamnoides, Hortonia floribunda, Humulus lupulus, Hydnocarpus kurzii, Hypericum perforaturn, Ilex paraguariensis, Illicium verum, Jasminum grandiflorum, Juniperus communis, Kigelia africana, Lagerstroemia indica, Lamium album, Larrea tridentata, Lavanda multifida, Lavanda penduculata, Lavanda pinnata, Lavanda stoechas, Lavanda viridis, Lavandula angustifolia, Lavandula latifolia, Leontopodium alpinum, Leptospermum scoparium, Limnanthes alba, Linum usitatissimum, Litchi sinensis, Lithospermum erythrorhizon, Lonicera* sp., *Luffa cylindrica, Malva sylvestris, Mangifera indica, Matricaria chamomilla, Medicago sativa, Melaleuca altemifolia, Melissa officinalis, Morinda citrifolia, Morus bombycis, Morus nigra, Nardostachys jatamansi, Nasturtium officinale, Oenothera biennis, Olea europaea, Oryza sativa, Padina pavonica, Paeonia albiflora, Paeonia suffruticosa, Palmaria palmata, Panax ginseng, Panicum miliaceum, Papaver somniferum, Passiflora incarnata, Pauffinia cupana, Pelargonium graveolens, Perilla frutescens, Perilla ocymoides, Persea gratissima, Persicaria hydroviper, Petroselinium crispum, Phyllanthus emblica, Picea abies, Pilocarpus jaborandi, Pinus lambertiana, Pinus sylvestris, Piper nigrum, Pistacia vera, Pisum sativum, Pogostemon cablin, Polygonum cuspidaturn, Portulaca oleracea, Prunella vulgaris, Prunus americana, Prunus amygdalus, Prunus armeniaca, Prunus domestica, Pueraria lobate, Punica granatum, Pyrus cydonia, Pyrus malus, Quercus infectoria, Ricinus communis, Robinia pseudoacacia, Rosa canina, Rosa centifolia, Rosa damascena, Rosa mosqueta, Rosa roxburghii, Rosa rubiginosa, Rosmarinus officinalis, Rubia* sp., *Rubus idaeus, Rubus occidentalis, Rubus ursinus, Ruscus aculeatus, Salix alba, Salix nigra, Salvia officinalis, Sambucus canadenses, Sambucus cerulea, Sambucus nigra, Sapindus mukurossi, Saponaria officinalis, Sargassum filipendula, Saxifraga sarmentosa, Saxifraga stolonifera, Schinus* sp., *Scutellaria baicalensis, Serenoa repens, Solanum ycopersicum, Solanum tuberosum, Solanum ycopersicum, Stryphnodendron* sp., *Symphytum officinale, Syzygium aromaticum, Tanacetum parthenium, Taraxacum officinale, Terminalia catappa, Terminalia sericea, Theobroma cacao, Thymus serpyllum, Thymus vulgaris, Tilia cordata, Trifolium pratense, Triticum aestivum, Tussilago farfara, Ulmus rubra, Uncaria tomentosa, Urtica dioica, Vaccinium macrocarpon, Vaccinium myrtillus, Valeriana officinalis, Vanilla planifolia, Viola tricolor, Vitis* sp., *Ximenia americana, Zanthoxylum piperitum, Zanthoxylum simulans, Zingiber officinale, Zingiber zerumbet, Ziziphus jujuba* or mixture of them.

In a preferred modality, the plant derivative is an extract is a hydroglycolic, glycolic or fluid extract.

In a preferred modality, the plant derivative is a hydroglycolic extract of *Calendula arvensis, Calendula bicolor, Calendula eckerleinii, Calendula lanzae, Calendula maderensis, Calendula maritima, Calendula maroccana, Calendula meuselii, Calendula officinalis, Calendula persica, Calendula stellate, Calendula suffruticosa, Calendula tripterocarpa* or mixtures of them.

In an even more preferred modality, the vegetable derivative is a hydroglycolic extract of *Calendula officinalis*.

In a more preferred modality, the present formulation is a hydroglycolic extract of *Calendula officinalis* with one or more excipients.

As an example of the extraction resulting from the formulation described here, it was observed that, in a formulation of *Calendula officinalis*, the reached content of triterpenoid monoesters in the plant derivative comprises the range of 0.0899-0.1868 mg/mL expressed in Lupeol, whereas the enriched fraction of the extraction by means of dichloromethane reveals 5.5% of calenduladiol monoesters, 15.7% of arnidiol monoesters and 35.2% of faradiol monoesters. The methodology used for quantification is through the High-Performance Liquid Chromatography (HPLC) platform.

In a preferred modality, biosurfactants are selected from monoramnolipids, dirhamnolipids, sophorolipids, mannosileritritol lipids, cellobiosis, xylolipids, trehalipids, lipopeptides, glycosides or parts of the molecule, such as rhamnose, or mixtures of them.

In one modality, the extracting agents are selected from, but without limitation to: water, ethyl alcohol from cereal, chloroform, ethanol, ethers, methanol, polyethylene glycols, propylene glycols, surfactants or a mixture of them.

In one modality, the surfactants suitable for use in the present formulation are those with a wide range of action and little irritability to human skin.

In a preferred modality, surfactants are selected from, but without limitation to: sulphonic acid, alkanolamides, ethoxylated alcohols and alkylphenols, alkyl polyglycosides, ethoxylated fatty amines, cetyltrimethylammonium bromide, benzalkonium chlorides, cetyltrimethylammonium chloride, cocamidopropyl betaine, coconut fatty acid diethanolamide, fatty acid esters, cyclic anhydrohexitoses esters, ethoxymines, sodium lauryl ether sulfate, ammonium lauryl sarcosinate, sodium lauroyl sarcosinate, ammonium lauryl sulfate, octoxynol, amine oxides, polyoxyethylene, tridecyl and surfactants: carboxymethylates, nonnitrogen cations; phosphates; organosiliconate; polymeric; ammonium quaternaries; sulfated; sulphonates or mixture of them.

The excipients present in the said formulation have one or more functions selected from: antioxidants, preservatives, precipitants, solvents and pH modulators (alkalizing or acidulating).

In one modality, excipients that have the antioxidant function are selected from, but without limitation to: alpha lipoic acid, ascorbic acid, citric acid, ellagic acid, ferulic acid, retinoic acid, anthocyanins, beta-carotenes, bisulfites, cysteine hydrochloride, flavonoids (quercetin, rutin, kaempferol, myricetin, hyperoside), hydroquinones, butylated hydroxyanisol (BHA), butylated hydroxytoluene (BHT), isothiocyanates, metabisulfites, polyphenols, propylgalates, resveratrol, sulfites, tannins, thioglycerol, thiols, thiosorbitol, tocopherols or a mixture of them.

In one modality, excipients, that have the preservative function, are selected from, but without limitation to: phenylmercury acetate, benzoic acid, boric acid, dehydroacetic acid, formic acid, propionic acid, salicylic acid, sorbic acid, undecylenic acid, benzyl alcohol, ethyl alcohol, phenethyl alcohol, benzylemiformal, benzylparaben, benzisothiazolinone, sodium benzoate, polyaminopropyl biguanide, sodium borate, domiphen bromide, bronidox, bronopol, iodopropynyl butylcarbamate, butylparaben, caprylyl glycol, clofucarban, chloramine-T, benzalkonium chloride, bezethonium chloride, silver chloride, chlorhexidine, chlorphenesin, chloroacetamide, chlorobutanol, chlorocresol, chlorophene, chloroxylenol, phenolic preservatives, sodium dehydroacetate, chlorhexidine diacetate, diazolidinyl urea, chlorhexidine dihydrochloride, chlorhexidine digluconate, dimethyloxazolidine, dioxanediol, hexamidine diisethionate, DMDM hydantoin, 2-bromo-2-nitropropane-1, ethylparaben, sodium orthophenyl phenol, phenoxyethanol, phenoxypropanol, glutaral, hexetidine, sodium hydroxymethylglycinate, hinokitiol, imidazolidinyl urea, sodium iodide, isobutylparaben, isopropylparaben, isothiazolinone, methenamine, methyldibromo glutaronitrile, methylparaben, nisin, nitronersol, o-cymen-5-OL, o-phenylphenol, p-Chloro-m-cresol, propylparaben, calcium propionate, sodium propionate, quaternium 15, quaternium 73, resorcinol, 7-ethylbicycloxazolidine, potassium sorbate, thimerosal, thymol or mixture of them.

In one modality, excipients that have the function of precipitating peptides are selected from, but without limitation to: acetic acid, polyacrylic acid, sulfosalicylic acid, trichloroacetic acid (TCA), sodium bicarbonate, carboxymethylcellulose (CMC), diethyl ether, chitosan, neutral salts, ammonium sulphate, methyl tert-butyl ether or mixture of them.

In a preferred modality, the pH of the formulation should be within the range of 4.5 to 10, but preferably 6 to 8.

In one modality, pH modulators, acidulating or alkalizing, can be used to adjust the pH of the formulation.

In a preferred modality, acidifying agents selected from, but without limitation to: ascetic acid, citric acid, ascorbic acid, adipic acid, phosphoric acid, glyoxylic acid, fumaric acid, lactic acid, lactobionic acid, malic acid, propionic acid, sorbic acid, succinic acid, tartaric acid, glucono-delta-lactone (GDL) or mixture of them.

In a preferred modality, the alkalinizing agents are selected from, but without limitation to: aminomethyl propanol, sodium bicarbonate, sodium borate, potassium citrate, sodium hydroxide, aluminum hydroxide, triethanolamine or mixture of them.

In a preferred modality, the formulation described can be used to obtain a product, as a cosmetic for protection, maintenance and balance of the natural regeneration of the skin, dermal mucous membrane and related parts or as a drug to accelerate the regeneration of the skin, dermal mucous membrane and related parts.

The formulation described is used as an Active Pharmaceutical Ingredient (API) for the preparation of a pharmaceutical product or a cosmetic product, both industrial and compounded.

The product can be of topic use, for example, in the form of presentation of a healing liquid for spray application, and may have other therapeutic applications, as indicated in the table below, as well as other forms of presentation, such as lotions, gels, creams and ointments. The target therapies for the finished product are chronic injuries and acute injuries that require accelerating the regeneration of the skin, dermal mucous membrane and related parts. The products that can be developed, from the said formulation, both in the pharmaceutical and in the cosmetic context, include the topical actions described in Tables 01 and 02, respectively, below:

TABLE 01

| TOPICAL PHARMACEUTICAL ACTIONS | | |
| --- | --- | --- |
| Acanthosis | Acrochordon | Mouth ulcers |
| Change of Pigmentation | Angioedema | Antiallergenic |
| Antibacterial or Bactericide | Antifungal or Antimycotic | Antihistamine |
| Antipruritic | Antivirals | Rashes |
| Bacteriostatic | Balanitis | Balanoposthitis |
| Bromhidrosis | Keratosis | Condyloma |
| Chromonychia | Dermatitis | Dyshidrosis |
| Ecthyma | Eczema | Ecchymosis |
| Erysipelas | Scabies | Scleroderma |
| Sporotrichosis | Fibrokeratoma | Fissures |
| Folliculitis | Furuncle | Gastroschisis |
| Gingivitis | Granuloma | Leprosy |
| Hemangioma | Hemorrhoid | Hidradenitis |
| Hydrocystoma | Hyperhidrosis | Hirsutism |
| Ichthyosis | Impetigo | Tinea |
| Mucous Membrane Lesions | Ophthalmic Injuries | Lupus |
| Melanoma | Myiasis | Omphalocele |
| Onychomycosis | Paronychia | Pediculosis |
| Pemphigus | Invertebrate Stings | Pityriasis |
| Rectal prolapse | Psoriasis | Burn |
| Keratosis | Radiodermatitis | Rosacea or Couperose |
| Seborrhea | Telangiectasia | Tungiasis |
| Urticaria | Xeroderma | Molluscum |

TABLE 2

| TOPICAL COSMETIC ACTIONS | | |
| --- | --- | --- |
| Acne | Expression Lines | Photoprotector |
| Astringent | Post-depilatory | Post-peeling |
| Anti-imperfections | Prevention of Keloids | Anti-age |
| Anti-wrinkle | Remineralizing | Antiperspirant |
| Soothing | Secative | Cellulitis |
| Make-up remover | Humectant | Disinfectant |
| Deodorant | Antioxidant | Oxidative stress |
| Exfoliating | Antiseptic agent | Barrier Function |
| Stretch marks | Capillary | Moisturizer |
| Homeostasis | Emollient | After-shave lotion |
| After-sun lotion | Sensitive skin | Rashes |

In an alternative modality, the product can be, but without limitation to: an after-sun lotion, a gel or protective cream for baby's rash, a healing liquid in the form of spray application, among others.

In a preferred modality, the product is a healing liquid with spray application, allowing the product to be sprayed more homogeneously and without contact with contamination sources, forming a biomolecular protective film, ensuring a more effective and safer treatment for the patient.

In a more preferred modality, the product is a high-performance healer, composed of 50% of the present formulation as API and 50% of a pharmaceutically acceptable vehicle, such as, for example, purified water, for spray application.

In one modality, the target therapy of the present formulation is for the regeneration of skin, dermal mucous membrane and related parts of any nature, more particularly for the treatment of any type of chronic or acute injury.

In a preferred modality, the target therapies of the present formulation are, but without limitation to, chronic injuries, which may be pressure injuries, venous ulcers and diabetic foot ulcers, as well as acute injuries, such as cuts in the skin due to trauma or by means of surgery, scratches, rashes and burns of any nature, including radiodermatitis and to accelerate the regeneration of the skin, dermal mucous membrane and related parts, such as omphalocele.

The product comprising the present formulation is a disruptive product, as it is practically the only product to be used end-to-end in the treatment of a chronic injury, and which can represent savings in the cost of a treatment of chronic injury, through a Home Care, hospital or outpatient system, among others, either due to the shorter treatment time or the less complex medical and nursing procedures. This situation also occurs in the treatment of an acute injury, with similar advantages, even considering the lower complexity of the treatment.

The use of the formulation of the present invention brings benefits and advantages such as:
- A lower cost of treatment: Because it has a lower cost than traditional drugs and products, treatment time is shorter, lower demand for health professionals (doctors and nurses) involved, as well as additional facilities and physical resources are not necessary.
- Treatment period reduced: It can decrease the treatment time from 30% to 40%, in the case of acute injuries, and, in case of chronic injuries, it can be greater than 50% reduction.
- Minimal complexity in treatment procedures: Due to the fact that the product, containing the present formulation, is liquid, for its application, it is enough to spray and let it dry. Changing a dressing using a product from the Advanced category on a chronic injury is 10 times longer than spray and letting the product containing the present formulation dry. In case of the Active product category, this relationship can be much higher, considering that there are dressings that require a surgeon, anesthetist and surgical center to apply the product, in addition to post-application procedures. It is worth mentioning that, in Home Care patients, recurrently, the application of the product's healing agent with the formulation of the present invention can be performed by the patient himself/herself or by a family caregiver, only with periodic supervision by healthcare professionals.

EXAMPLES

The following examples demonstrate preferred implementations of the present invention. However, it should be noted that these examples have the sole purpose of illustrating the invention and should not be considered as limitations, since many variations of them are possible without, with this, reducing or restricting the scope of the invention.

Example 1

A preferred modality of the formulation of the present invention is described below, which can be used as an API in the preparation of a final product for the regeneration of the skin, dermal mucosa and related parts.

TABLE 03A

FORMULATION EXAMPLE COMPRISING VEGETABLE EXTRACT, EXTRACTING AGENTS, BIOSURFACTANT AND EXCIPIENTS

| ITEM | INGREDIENT | FUNCTION | TECHNICAL NAME | RANGE - COMPOSITION (%) | PREFERRED COMPOSITION (%) | UNIT |
|---|---|---|---|---|---|---|
| 1 | Purified Water. | Solvent | — | | q.s.p | mL |
| 2 | Calendula flower (powder) | Herbal drug | *Calendula officinalis* L. | 2-6 | 4 | g |
| 3 | Methylparaben | Preservative | — | 0.02-0.27 | 0.18 | g |
| 4 | Propylparaben | Preservative | — | 0.01-0.05 | 0.02 | g |
| 5 | Sodium Bicarbonate | Precipitating | — | 2-8 | 5 | g |
| 6 | Ethyl Alcohol from Cereals | Extractor | — | 5-35 | 22 | mL |
| 7 | PEG | Extractor | Polyethylene glycol 400 | 2-12 | 6 | g |
| 8 | A90 | Extractor | Amide 90 | 0.2-4 | 0.8 | g |
| 9 | JBR 425 | Extractor | Monoramnolipids and Dirhamnolipids | 0.1-5 | 0.4 | g |
| 10 | CAPB | Extractor | Cocamidopropyl Betaine | 0.4-3 | 0.8 | g |
| 11 | SLS | Extractor | Sodium Lauroyl Sarcosinate | 0.1-1.2 | 0.6 | g |
| 12 | Triton X 100 | Extractor | Octoxynol | 0.2-2.0 | 0.9 | g |
| 13 | SLES | Extractor | Sodium Lauryl Ether Sulfate | 0.1-5.0 | 1.5 | g |
| 14 | Quercetin (C.I. Natural Yellow 10) | Antioxidant | — | 0.05-2.50 | 0.134 | g |
| 15 | Ascorbic acid | Antioxidant | — | 0.1-4.0 | 0.3 | g |
| 16 | Citric acid/ Sodium Bicarbonate | PH adjustment | — | 0.0-4.0 | ** | g |

**Sufficient amount for pH adjustment

TABLE 03B

EXAMPLE OF PRODUCT FORMULATION PLENUSDERMAX®

| ITEM | INGREDIENT | FUNCTION | TECHNICAL NAME | COMPOSITION (%) | UNIT |
|---|---|---|---|---|---|
| 1 | Purified Water. | Solvent | — | q.s.p | mL |
| 2 | Calendula flower (powder) | Herbal drug | Calendula officinalis L. | 4 | g |
| 3 | BHT | Antioxidant | Butylated Hydroxytoluene | 0.02 | g |
| 4 | Sodium Bicarbonate | Precipitator | — | 6 | g |
| 5 | Ethyl Alcohol from Cereals | Extractor | — | 20 | mL |
| 6 | Phenoxyethanol/ Caplylglycol | Preservative | — | 1 | g |
| 7 | Polyethylene glycol | Extractor | — | 12 | g |

Tests

Tests carried out in vitro and in vivo demonstrate that the formulation of the present invention has a superiority in terms of accelerating the healing process compared to other formulations.

Test 1—Analysis of the Healing Potential Through the Human Fibroblast Migration In Vitro Assay (Scratch Assay) in Formulations Based on Calendula Hydroglycolic Extracts Three formulations were used, as follows:

1. Formulation according to the preferred composition of Table 03A with pH 6 (Product A) that integrates the formulation of the present invention;
2. Formulation according to the preferred composition of Table 03A with pH 8 (Product B) that integrates the formulation of the present invention;
3. Plenusdermax® (Product C), according to the composition of Table 03B.

As controls were used:
Control (mitomycin);
Medium (positive control).

For the manufacture of Plenusdermax® (Product C) it was used according to definition of Table 03B.

All treatment conditions (formulations) were incubated with mitomycin and, thus, comparisons were made in relation to the control (mitomycin).

The Medium (positive control) condition, without treatment, was used as an internal quality parameter and perfectly met the requirements. The Medium condition (positive control) was not used for no comparisons of results.

FIG. 1 represents the flow chart of the cell migration test, in which human fibroblasts are plate replicated (HFF1), after 24 h the scratching and image capture is performed. Then, it is incubated with 0.02% of the treatment (formulations), concentration stipulated according to the cytotoxicity analysis, which was greater than 80% of cell viability. The analysis protocol followed was according to the teachings of Coecke S, Balls M, Bowe G, Davis J, Gstraunthaler G, Hartung T, Hay R, Merten O W, Price A, Schechtman L, Stacey G, Stokes W. *Guidance on Good Cell Culture Practice. A Report of the Second ECVAM Task Force on Good Cell Culture Practice. Altern Lab Anim.* 33(3):261-87, 2005.

From the raw data of the pixel count of the scratching area, the Closing Area and the Closing Percentage (%) are calculated, the first measurement being the difference of the pixel count of the scratching area at zero time in relation to 24 hours, after incubation under experimental conditions, and the second measurement, by means of the proportional relationship of the Closing Area at 24 hours related to the Closing Area at zero time, being considered the initial area at zero time equal to 100%.

For the analysis of outliers, the Multivariated Robust Outliers (Mahalanobis distance) method (MAHALANOBIS, 1936; FARBER & KADMON, 2003, AGGARWAL, 2017) was used, using the JMP v.14 program. The statistical analysis adopted the One-way ANOVA method using the Student's t-test, comparing all conditions among themselves, considering the value of $\alpha = 0.05$.

The maximum values of Closing Percentage, for each experimental condition of the products, were used in the analysis of hierarchical grouping, using the Ward method and calculations of the FoldChange, considering the ratio between the desired conditions.

45 tests were carried out: experimental and technical triplicates of the 5 different conditions tested, being 3 formulations and 2 controls. Table 04 shows the gross values and their respective values of Closing Area and Closing Percentage.

Figure 2:
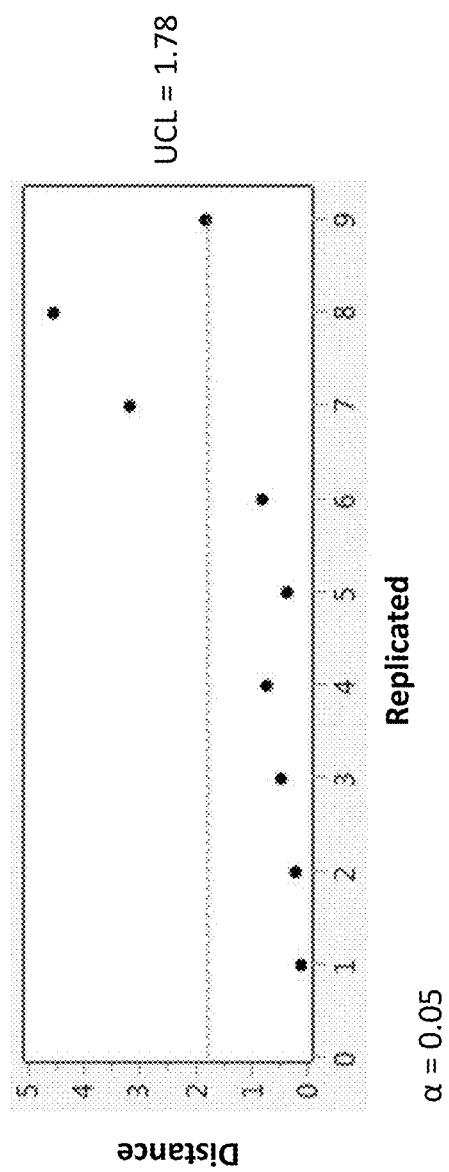
FIG. 2—Distribution chart of the Mahalanobis distance values of the nine replicates for the experimental condition of Product B. On the x-axis, representing each of the nine replicates and the y-axis, the obtained distance values. The blue line determines the threshold value (upper control limit) used to determine the outliers in the analysis, with replicates with values above the limit excluded from the analyzes. Being UCL=1.78 and α=0.05.

FIG. 2 shows the distribution chart of the distance values, based on the Closing Percentage data for the condition Product B, in order to determine the possible outliers using the Mahalanobis distance method.

For each condition, a threshold value was calculated, referred to as UCL (Upper Control Limit), used to identify and select the replicates that were considered outliers in the data. Replicates with values above the limit were excluded from the analyzes.

TABLE 4

TABLE CONTAINING THE GROSS VALUES AND THEIR RESPECTIVE CALCULATED VALUES OF CLOSING AREA AND CLOSING PERCENTAGE

| Assay No. | Experimental Conditions | Area (pixels) Time = 0 h | Area (pixels) Time = 24 h | Experimental Replicate | Technical Replicate | Closing area (pixels) | % of closing |
|---|---|---|---|---|---|---|---|
| 1 | MEDIUM | 3770418 | 2454495 | 1 | 1 | 1315923 | 34.90124968 |
| 2 | MEDIUM | 3908607 | 2229492 | 1 | 2 | 1679115 | 42.95942263 |
| 3 | MEDIUM | 4207031 | 2847176 | 1 | 3 | 1359855 | 32.32338911 |
| 4 | MEDIUM | 3287791 | 2063209 | 2 | 1 | 1224582 | 37.24634565 |
| 5 | MEDIUM | 3277054 | 1796003 | 2 | 2 | 1481051 | 45.19458636 |
| 9 | MEDIUM | 3947272 | 2501676 | 3 | 3 | 1445596 | 36.6226599 |
| 10 | CONTROL | 3995113 | 2956334 | 1 | 1 | 1038779 | 26.00124202 |
| 11 | CONTROL | 3209271 | 2168365 | 1 | 2 | 1040906 | 32.43434412 |
| 12 | CONTROL | 3486143 | 2769599 | 1 | 3 | 716544 | 20.55406218 |
| 15 | CONTROL | 3864172 | 2494765 | 2 | 3 | 1369407 | 35.43856226 |
| 17 | CONTROL | 4357640 | 2995728 | 3 | 2 | 1361912 | 31.25343076 |

TABLE 4-continued

TABLE CONTAINING THE GROSS VALUES AND THEIR RESPECTIVE
CALCULATED VALUES OF CLOSING AREA AND CLOSING PERCENTAGE

| Assay No. | Experimental Conditions | Area (pixels) Time = 0 h | Area (pixels) Time = 24 h | Experimental Replicate | Technical Replicate | Closing area (pixels) | % of closing |
|---|---|---|---|---|---|---|---|
| 18 | CONTROL | 3991683 | 2621873 | 3 | 3 | 1369810 | 34.3166028 |
| 19 | Product B | 3070391 | 1762955 | 1 | 1 | 1307436 | 42.58206854 |
| 20 | Product B | 3520111 | 2134691 | 1 | 2 | 1385420 | 39.35728163 |
| 23 | Product B | 3154684 | 1727477 | 2 | 2 | 1427207 | 45.24088625 |
| 24 | Product B | 2920742 | 1461052 | 2 | 3 | 1459690 | 49.97668401 |
| 25 | Product B | 3031079 | 758108 | 3 | 1 | 2272971 | 74.98884061 |
| 27 | Product B | 3010369 | 1184201 | 3 | 3 | 1826168 | 60.66259651 |
| 28 | Product C | 3426711 | 1910916 | 1 | 1 | 1515795 | 44.23469035 |
| 29 | Product C | 3600411 | 2091502 | 1 | 2 | 1508909 | 41.90935424 |
| 30 | Product C | 3100026 | 1877302 | 1 | 3 | 1222724 | 39.44237887 |
| 32 | Product C | 3713794 | 2126546 | 2 | 2 | 1587248 | 42.73925802 |
| 33 | Product C | 3531861 | 2064338 | 2 | 3 | 1467523 | 41.55098403 |
| 34 | Product C | 2785597 | 1250057 | 3 | 1 | 1535540 | 55.12426959 |
| 38 | Product A | 3657583 | 2225033 | 1 | 2 | 1432550 | 39.1665753 |
| 41 | Product A | 3007332 | 1789327 | 2 | 2 | 1218005 | 40.50118178 |
| 42 | Product A | 3327913 | 1792002 | 2 | 3 | 1535911 | 46.15237838 |
| 43 | Product A | 3668218 | 1801983 | 3 | 1 | 1866235 | 50.8757931 |
| 44 | Product A | 3019565 | 400573 | 3 | 2 | 2618992 | 86.73408256 |
| 45 | Product A | 3459147 | 1910901 | 3 | 3 | 1548246 | 44.7580285 |

The experimental conditions (Products) tested that were identified with a significant difference in relation to the control group were: Product A and Product B.

Figure 3:
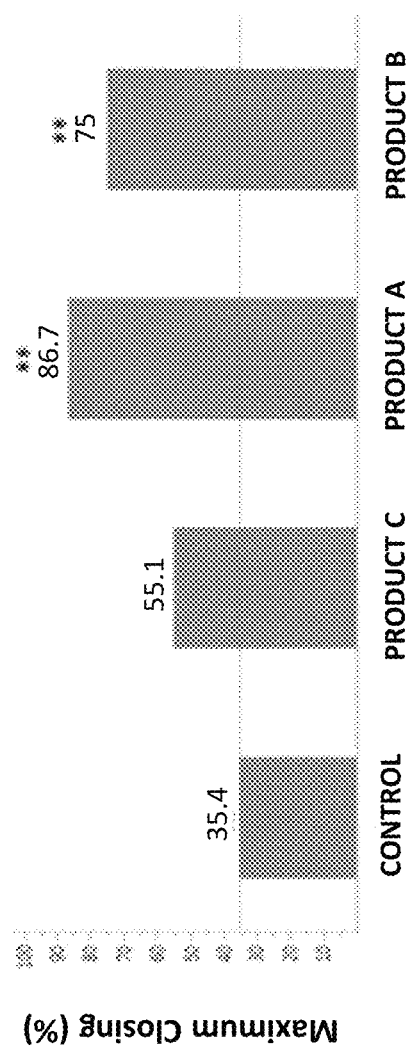
FIG. 3—Evaluation of the healing potential through cell migration. Distribution chart of Maximum Closing Percentage in relation to the experimental conditions tested. The horizontal line shows the limit for the control condition. (**) p<0.01 (Student's t-test).

The significance values and the maximum Closing Percentage (%) for all experimental conditions tested in relation to the control group are illustrated in FIG. 3 and Table 05.

Table 05 presents the conditions classified in a decreasing way in relation to the maximum value of Closing Percentage. In Tables 06, 07 and 08 are all the comparative analyzes between Products and their respective significance values.

TABLE 05

FOLDCHANGE VALUES OBTAINED FOR EACH COMPARISON

| | Product A | Product B | Product C | CONTROL |
|---|---|---|---|---|
| Product A | 1 | — | — | — |
| Product B | 1.16 | 1 | — | — |
| Product C | 1.57 | 1.36 | 1 | — |
| CONTROL | 2.45 | 2.12 | 1.56 | 1 |

NOTE:
the FoldChange value was calculated based on the ratio between the conditions (condition on the x axis/condition on they axis) using the values of maximum Closing Percentage.

TABLE 06

STATISTICAL ANALYSIS OF FORMULATIONS IN RELATIONSHIP TO THE CONTROL GROUP - COMPARISON FOR EACH PAIR USING STUDENT'S T-TEST - LEAST SIGNIFICANT DIFFERENCE (LSD) THRESHOLD MATRIX

| Abs(Dif)-LSD | Product A | Product B | Product C | CONTROL |
|---|---|---|---|---|
| Product C | −6.302 | −7.072 | −14.270 | −0.103 |
| CONTROL | 7.865 | 7.095 | −0.103 | −14.270 |

Positive values show pairs of mediums that are significantly different

TABLE 07

STATISTICAL ANALYSIS OF FORMULATIONS IN RELATION TO THE CONTROL GROUP - COMPARISON FOR EACH PAIR USING STUDENT'S T-TEST - LETTER CONNECTION REPORT

| Level | | | Average |
|---|---|---|---|
| Product A | A | | 52.134726 |
| Product B | A | | 51.364673 |
| Product C | A | B | 44.166823 |
| CONTROL | | B | 29.999707 |

Levels not connected by the same letter are significantly different

TABLE 08

STATISTICAL ANALYSIS OF FORMULATIONS IN RELATION TO THE CONTROL GROUP - COMPARISON FOR EACH PAIR USING STUDENT'S T-TEST-REPORT OF ORDERED DIFFERENCES

| Level | -Level | Difference | Difference of standard error | Lower confidence limit | Higher confidence limit | p-value |
|---|---|---|---|---|---|---|
| Product A | Control | 22.13502 | 6.840911 | 7.8651 | 36.40491 | 0.0041* |
| Product B | Control | 21.36497 | 6.840911 | 7.0951 | 35.63486 | 0.0054* |
| Product C | Control | 14.16712 | 6.840911 | −0.1028 | 28.43701 | 0.0515 |

According to the classification of the maximum closing values obtained for each experimental condition (Table 09), the formulations that best performed the migration process to the scratching area were: Product A and Product B, these being the formulations that showed a significant difference in relation to the control.

TABLE 09

CLASSIFICATION OF EXPERIMENTAL CONDITIONS
IN RELATION TO THE MAXIMUM CLOSING PERCENTAGE

| Ranking | Conditions (Products) | p-Value | % of closing (Maximum value) |
|---|---|---|---|
| 1$^{st}$ | Product A | 0.0054 | 86.73 |
| 2$^{nd}$ | Product B | 0.0041 | 74.98 |
| 3° | Product C | 0.0515 | 55.1 |

NOTE:
The values of significant difference were calculated using the Student's t-test in relation to the control condition, $\alpha = 0.05$.

The analysis of the differences observed between the conditions were evaluated and the FoldChange values calculated (Table 05) showed an increase in migration, compared to the control, of 2.45 times by Product A and 2.12 times by Product B. in relation to product C (Plenusdermax®) the FoldChange values for Products A and B were 1.57 times and 1.36 times higher, respectively. The metrics used in the statistical analysis of the comparisons between the different formulations in relation to the control group are shown in Tables 06, 07 and 08.

Figure 4:
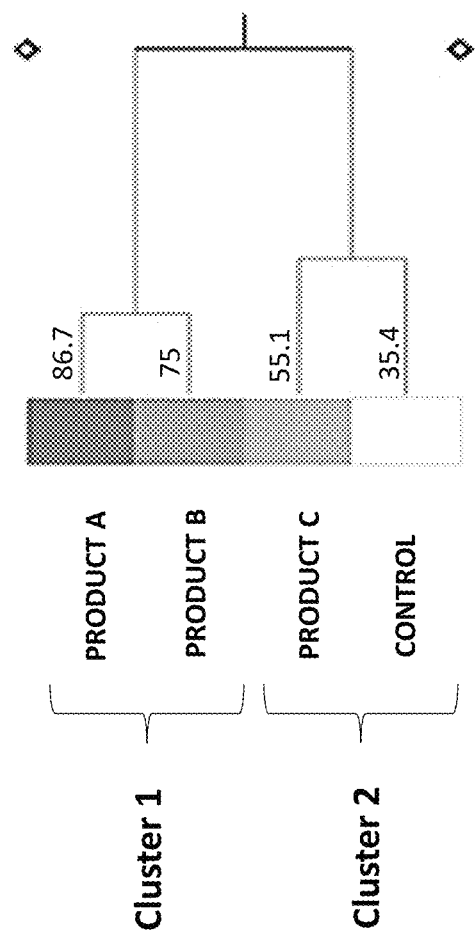
FIG. 4—Dendrogram of the experimental conditions resulting from the hierarchical cluster analysis. The maximum values of Closing Percentage for each condition were used for the construction of the tree diagram. The diamonds indicate the distance limit (graph below the Dendrogram) used to define the number of clusters (2) in the analysis.

The hierarchical clustering analysis resulted in the formation of 2 distinct clusters, according to the variations in Closing Percentage obtained between the treatment conditions (Products) (FIG. 4). So we the clusters are formed in the following way:
  I. Cluster 1: Product A and Product B;
  II. Cluster 2: Product C (Plenusdermax®) and Control.

The comparative statistical analysis between the different clusters shows significant differences in relation to the Closing Percentage, p=0.0049. The metrics used in the statistical analysis of comparisons between clusters are shown in Table 10.

TABLE 10

STATISTICAL ANALYSIS BETWEEN THE CLUSTERS FORMED
THROUGH THE HIERARCHICAL GROUPING ANALYSIS -
ONE-WAY ANALYSIS OF CLOSING % BY STUDENT'S
T-TEST, ASSUMING UNEQUAL VARIATIONS

| Difference | −14.666 | Proportion test | −2.88483 |
|---|---|---|---|
| Difference of standard error | 5.084 | Degree of freedom | 18.14351 |
| Higher confidence limit | −3.991 | Prob > \|t\| | 0.0098* |
| Lower confidence limit | −25.341 | Prob > t | 0.9951 |
| Confidence | 0.95 | Prob < t | 0.0049* |

The statistical analyzes of each condition (Product) showed significant differences in the percentage of Closing scratching in relation to the control group, which reflects the effectiveness of migration of fibroblasts to scratching. These formulations (Products) were subsequently classified according to the maximum value of Closing Percentage obtained in the analyzes, showing Product A as the formulation that obtained the best performance, followed by Product B. Followed by Product C, Plenusdermax®.

Observing the comparative FoldChange values between the Product A and Product B formulations in relation to the Product C formulation, there was a difference of 57% and 36%, respectively, of an increase in the in vitro cicatrization process (cell migration) for the formulations (Table 5) using the maximum closing percentages obtained.

Figure 5:
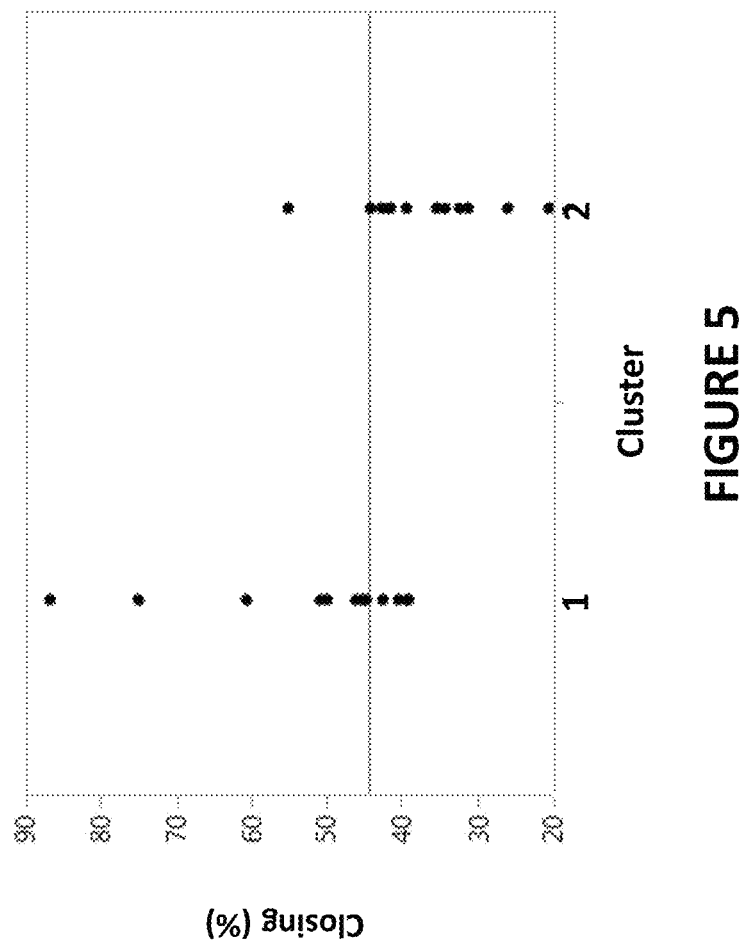
FIG. 5—Box plot of the distribution of closing % data by cluster. Cluster 1 is formed by products A and B, cluster 2 is formed by Product C and Control condition.
Figure 6:
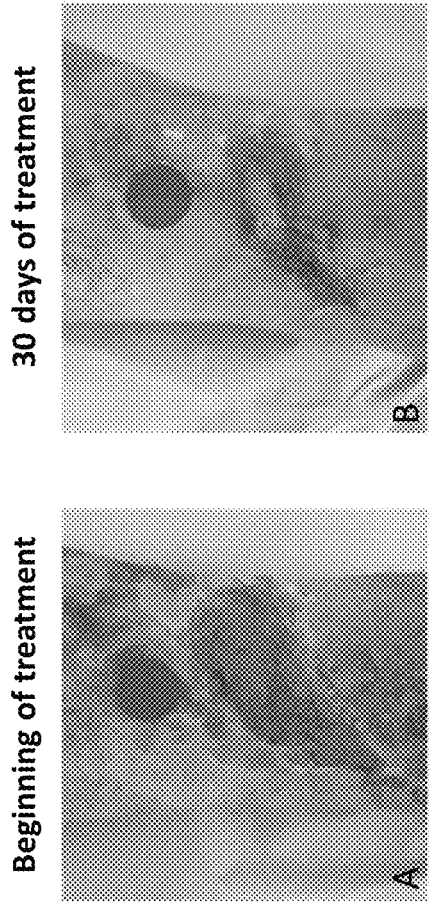
FIG. 6—Venous ulcer, photographed before (A) and after (B) the treatment with the product of the present invention, which consists of the tested Product B, with the template in blue (LCC patient).
Figure 7:
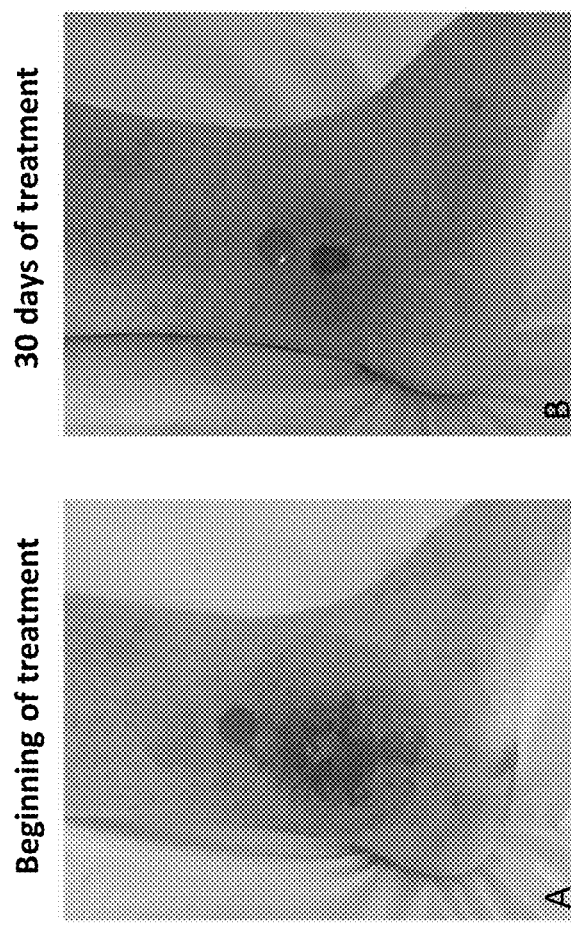
FIG. 7—Venous ulcer, photographed before (A) and after (B) the treatment with the product of the present invention, which consists of the tested Product B, with the template in blue (CAC patient).
Figure 8:
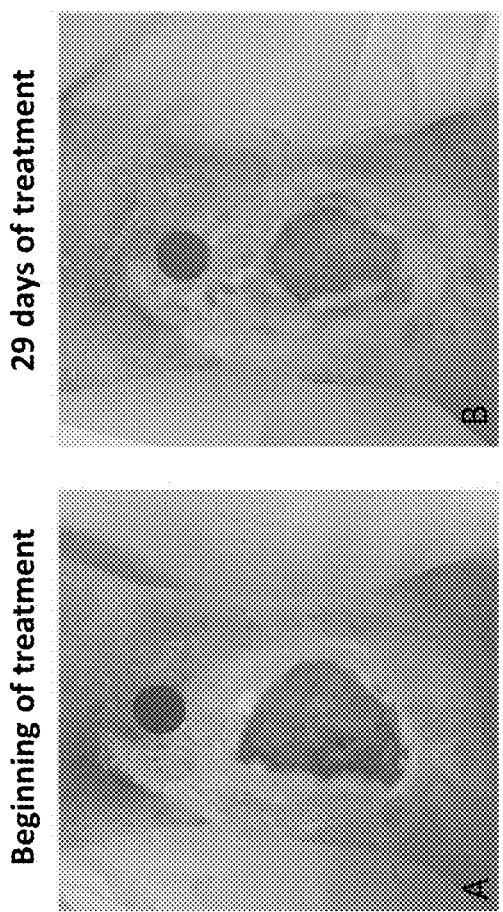
FIG. 8—Venous ulcer, photographed before (A) and after (B) treatment with a product based on the product of the present invention, which consists of the Product B tested, with the template in blue (VBSS patient).
Figure 9:
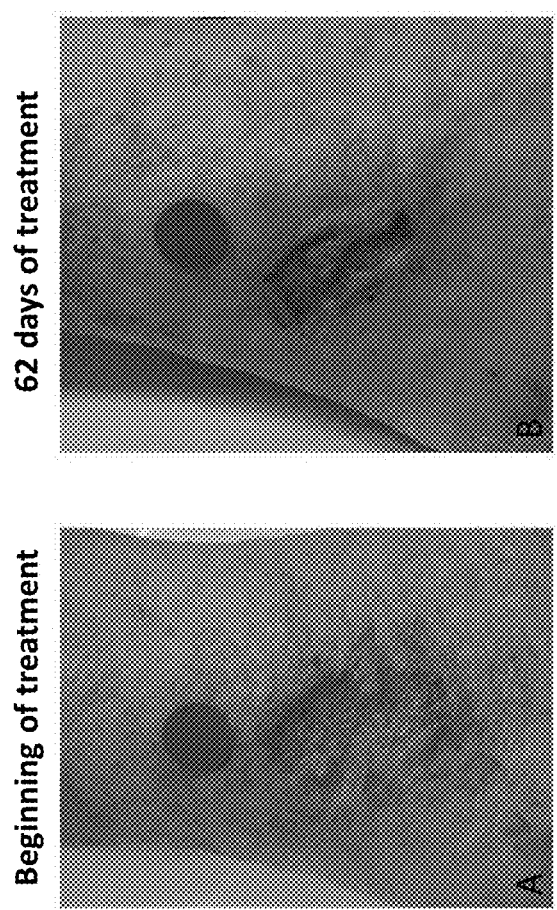
FIG. 9—Venous ulcer, photographed before (A) and after (B) treatment with a product based on the product of the present invention, which consists of the Product B tested, with the template in blue (RMM patient).

Ward's method was used for cluster analysis to show which formulations (Products) presented the same performance in the in vitro cicatrization process (cell migration). The products that stood out and were grouped according to their performance were the formulations Product A and Product B, belonging to cluster 1 (FIG. 3 and FIG. 5).

These results show that the balance of the components of the formula, together with the extracting agents and with the bioactive (triterpenoid monoesters) produced unique and effective formulations in the in vitro cicatrization process, as seen through the statistical analysis shown in Table 9.

The effectiveness test of analysis of the in vitro cicatrization process (scratch assay) used to evaluate the formulations regarding the Closing Percentage revealed two formulations with potential to accelerate the process of cell migration. The formulations that stood out and, significantly, were different related to the control were: Product A and Product B. The Product A and Product B formulations were the most promising and most effective in relation to the Product C formulation tested.

The balance of the components of the formula together with the extracting agents together and with the bioactive (triterpenoid monoesters) present in Product A and Product B led to the acceleration of the in vitro cicatrization process, which, compared to Product C, is 57% and 36% higher, respectively.

Test 2—Evaluation of the Healing Activity of the Formulation of the Present Invention Based on Differentiated Plant Extract from Effective Technology Containing Bioactive from the Medicinal Plant *Calendula officinalis* L. In Venous Ulcers Through a clinical study it was possible to compare the healing activity in lesions of patients with venous ulcers treated with the product based on the present invention (Product B) in relation to the treatment with Product C.

The patients' inclusion criteria were:
  be over 18 years old;
  not having a medical diagnosis of arterial or mixed ulcers;
  not having a medical diagnosis of severe malnutrition, severe anemia;
  not be a smoker, alcoholic or drug addict;
  not having an infection treated with broad-spectrum antibiotic therapy;
  have no necrosis in the lesion and have no adverse reaction to medicinal plant-based products from the Asteraceae family.

Exclusion criteria were:
  not apply the dressing according to the protocol;
  use another product in the injury in addition to that which is prescribed;
  not to attend the scheduled appointments.

The healing product based on Product B (1:1 dilution in ultrapure water) has a liquid presentation, being applied topically by spray twice a day, by the patient or his/her caregiver, at home.

During the first appointment, healthcare professionals, participants in the clinical study, guide and carry out, step by step, the application procedure and dressing changes. Initially, the wound is cleaned with saline solution, followed by the application of the product and total drying of the product on the wound course.

After drying, the wound is covered with a physical dressing (non-adherent gauze) and bandage. It is recommended to perform this procedure twice a day until the patient returns for periodic reviews and medical follow-up every 30 days.

At each patient visit, the lesions were photographed, according to criteria of preservation of the research subject's privacy, as well as measured, using the applications of the Image J Program (Distribution of the National Institute of Health (NIH) of the USA), using a template specific for the normalization of areas when measurements are made.

In order to measure the lesion, photos were taken with photographic equipment, with a resolution of 13 megapixels and which, after collecting the image, are accessed by the Image J Program to evaluate the border of the wound and count the pixels by region.

1. Photography criteria:
    a. The lesion should be photographed with a template next to the wound. The template is 1.5 cm in diameter (176.714587 mm$^2$), adhesive, disposable and allows to correct differences in brightness and distances.
    b. Subsequent photographs must use the same type of template, always with a minimum resolution of 5 megapixels, without using the approximation feature;
    c. Photos must be taken perpendicular to the lesions, at a distance of approximately 50 cm;
2. The program used for image processing and analysis is IMAGE J, of public domain.
3. Calculation of the lesion wound area: For the calculation of the wound area, we have, according to Table 11, that:

TABLE 11

CALCULATION OF THE WOUND AREA
Calculation of the wound area

| Template Area (pixels) | Template Area (mm$^2$) |
|---|---|
| AGP | 176.714587 |
| Wound area (pixels) | Wound area (mm$^2$) |
| ALP | AL |

Formulation: $AL=(176.714587 \times ALP)/AGP$

The contraction value of the wound is calculated in square millimeters (mm$^2$) every week (CLs), using the difference of the initial area of the wound (Ia) in relation to the final area of the lesion (Fa) divided by the time elapsed between the images obtained, in weeks. The calculation of the reduction percentage per week (% RE/wk) is made using the formula below:

$$\% RE/wk = (CLs/Ia) \times 100$$

The comparative analyzes take place by combining the mean values obtained from the contraction of the wound per week (CLs) and the percentage of the healing speed per week (% RE/wk), between the different parameters. The method used is the Student's t-test and using the GraphPad Prism program. Values of p<0.05 are considered statistically significant.

Eleven patients were recruited, totaling 12 injuries. The values obtained by planimetry, from the measurement of the healing area of the 12 injuries, are shown in Table 12.

TABLE 12

QUANTITATIVE DATA OBTAINED FROM PLANIMETRY ANALYSIS.

| Patient | TLAT (days) | Initial Area (mm$^2$) | Final Area (mm$^2$) | Treatment (days) | Treatment (weeks) | CLs | % RE/wk |
|---|---|---|---|---|---|---|---|
| LCC | 545.0 | 898.5 | 89.2 | 30.0 | 4.3 | 188.8 | 21.0 |
| RPK | 485.0 | 1396.3 | 880.6 | 23.0 | 3.3 | 157.0 | 11.2 |
| VBSS | 730.0 | 1308.2 | 790.9 | 29.0 | 4.1 | 124.9 | 9.5 |
| ALL | 1825.0 | 1578.2 | 799.3 | 60.0 | 8.6 | 90.9 | 5.8 |
| AGG | 730.0 | 2055.9 | 1277.2 | 95.0 | 13.6 | 57.4 | 2.8 |
| RMM | 1825.0 | 702.5 | 221.6 | 62.0 | 8.9 | 54.3 | 7.7 |
| GLO | 730.0 | 652.1 | 424.1 | 32.0 | 4.6 | 49.9 | 7.6 |
| ATC | 10950.0 | 863.7 | 638.5 | 35.0 | 5.0 | 45.0 | 5.2 |
| NSH-2 | 1095.0 | 517.2 | 5.3 | 105.0 | 15.0 | 34.1 | 6.6 |
| CAC | 240.0 | 137.8 | 0.0 | 30.0 | 4.3 | 32.2 | 23.3 |
| DRD | 180.0 | 264.3 | 38.9 | 51.0 | 7.3 | 30.9 | 11.7 |
| NSH-1 | 1095.0 | 794.1 | 355.3 | 105.0 | 15.0 | 29.3 | 3.7 |
| Average | 1702.5 | 930.7 | 460.1 | 54.8 | 7.8 | 74.5 | 9.7 |
| Standard Deviation | 2960.4 | 559.4 | 416.0 | 31.0 | 4.4 | 54.1 | 6.5 |

The mean value of the wound contraction for the 12 studied cases of venous ulcers treated on the basis of Product B was 74.5 mm$^2$ per week, which corresponds to 10.6 mm$^2$ per day. The average reduction percentage obtained was 9.7 mm$^2$ per week or 1.4 mm$^2$ per day. The maximum and minimum values for the wound contraction per week were 188.8 mm$^2$ and 29.3 mm$^2$. The maximum and minimum values for the reduction percentage per week were 23.3% and 2.8%, respectively.

FIGS. 6 to 9 exemplify four cases of treatment with the product based on Product B.

The comparative analysis of the results obtained from the new formulation of Product B in relation to Product C, was carried out using data from the publication of Buzzi et al. in 2016, in which the healing effectiveness was analyzed in patients with venous ulcers, using the Product C. The data obtained by Buzzi's study and the comparative analysis of the new Product B are illustrated in Table 13.

TABLE 13

COMPARATIVE ANALYSIS OF THE VALUES OF WOUND CONTRACTION (mm$^2$/WEEK) OF THE DIFFERENT FORMULATIONS TESTED IN PATIENTS WITH VENOUS ULCER

| Treatment Conditions | N | Average | Median | Interval | SD | P-Value |
|---|---|---|---|---|---|---|
| Product C | 38 | 42.7 | 34.7 | 5.5-110.2 | 28.15 | 0.0099 |
| Product B | 12 | 74.5 | 52.1 | 293-188.8 | 54.1 | |

Note:
The values referring to the Product C treatment condition were obtained from the work of Buzzi et al. in 2016[18]. The significance value (P-Value) was calculated from comparisons of the mean values of wound contraction (mm$^2$/week) of the different formulations using the student's t-test, p <0.05.

The comparative analysis showed a significant difference (p=0.0099) in the contraction of the venous lesion between the analyzed products. The formulation based on Product B showed the greatest contraction per week, with an average value of 74.5 mm$^2$, compared to Product C, which had an average value of 42.7 mm$^2$.

The comparative analysis showed a significant difference between the formulations, observing that it was 1.74 (74%) times higher for the contraction (mm$^2$/week) with the use of the product based on Product B in relation to Product C.

Conclusion of the Tests

Based on the two tests presented, it can be concluded that:
The effectiveness test of analysis of the in vitro cicatrization process (scratch assay) used to evaluate the three formulations regarding the Closing Percentage revealed two formulations with potential to accelerate the process of cell migration. The formulations that stood out and, significantly, were different related to the control were: Product A and Product B. The formulations Product A and Product B are new formulations called Product A and Product B, and were the most promising and most effective in relation to the other formulations tested, including when compared to Product C;

The balance of the components of the formula together with the extracting agents and with the bioactive (triterpenoid monoesters) present in Product B led to the acceleration of the in vitro cicatrization process, which, compared to Product C, proved to be 57% higher;

Product B demonstrated high efficacy in reducing injuries to patients with venous ulcers;

The average value of contraction was 74.5 mm$^2$ per week, with the average reduction percentage obtained being 9.7% per week;

The comparative analysis showed a significant difference between the formulations, observing that it was 74% higher for the contraction (mm$^2$/week) with the use of the product based on Product B in relation to Product C.

After described examples of preferred implementations, it should be understood that the scope of the present invention encompasses other possible variations, being limited only by the content of the appended claims, including the possible equivalents.

The invention claimed is:

1. A topical pharmaceutical formulation comprising:
at least one medicinal plant, part or extract thereof which is a source of triterpenoid monoesters,
two or more extracting agents, wherein at least one extracting agent is a biosurfactant;
and one or more pharmaceutically acceptable excipients selected from antioxidants and precipitants;
one or more preservatives; and
one or more pH modulators,
wherein the formulation has a pH in the range of 4.5 to 10.

2. The formulation according to claim 1, wherein the medicinal plant, part or extract is selected from the group consisting of *Acacia senegal, Achillea millefolium, Aesculus hippocastanum, Agrimonia eupatoria, Ajuga turkestanica, Alcea rosea, Alchemilla vulgaris, Aleurites moluccana, Aloe barbadensis, Aloe vera, Althaea officinalis, Ammi visnaga, Ananas sativus, Anethum graveolens, Angelica archangelica, Anthemis nobilis, Arachis hypogaea, Arctium lappa, Arctostaphylos sp., Argania spinosa, Arnica montana, Artemisia absinthium, Artemisia capillaris, Artemisia vulgaris, Ascophyllum nodosum, Astragalus membranaceus, Astragalus sinicus, Atractylodes lancea, Avena sp., BeIlls perennis, Berberis aristata, Berberis vulgaris, Bertholletia excelsa, Beta vulgaris, Betula alba, Boerhavia difusa, Borago officinalis, Boswellia carterii, Brassica campestres, Brassica oleracea, Brassica rapa, Buddleja davidii, Bupleurum falcatum, Butyrospermum parkii, Buxus chinensis, Calendula arvensis, Calendula bicolor, Calendula eckerleinii, Calendula lanzae, Calendula maderensis, Calendula maritima, Calendula maroccana, Calendula meuselii, Calendula officinalis, Calendula persica, Calendula stellata, Calendula suffruticosa, Calendula tripterocarpa, Calluna vulgaris, Calophyllum inophyllum, Camellia japonica, Camellia oleifera, Camellia sinensis, Cannabis sativa, Carthamus tinctorius, Carya illinoensis, Castanea sativa, Cedrus atlantica, Centaurea cyanus, Centella asiatica, Chamaemelum nobile, Chamomilla recutita, Chondrus crispus, Citrullus colocynthis, Citrus aurantifolia, Citrus aurantium, Citrus medica, Citrus unshiu, Coffea arabica, Cola acuminata, Coleus barbatus, Commiphora myrrha, Copaifera officinalis, Copernicia cerifera, Cornus sp., Corylus americana, Corylus avellana, Crataegus monogyna, Cucumis melo, Cucumis sativus, Cucurbita pepo, Curcuma longa, Cymbopogon citratus, Cymbopogon martini, Diplolepis rosae, Echinacea purpurea, Elaeis guineenses, Epilobium sp., Equisetum arvense, Eriobotrya japonica, Eucalyptus sp., Eugenia aromatica, Eugenia caryophyllus, Euphorbia cerifera, Euphrasia officinalis, Euterpe oleracea, Evodia rutaecarpa, Fagus sylvatica, Filipendula glaberrima, Filipendula rubra, Filipendula ulmaria, Fucus vesiculosus, Gardenia jasminoides, Gentiana lutea, Geranium pratense, Ginkgo biloba, Glyzyrrhiza glabra, Gossypium herbaceum, Hamamelis sp., Hapagophytum procumbens, Helianthus annuus, Hibiscus sp., Hippophae rhamnoides, Hortonia floribunda, Humulus lupulus, Hydnocarpus kurzii, Hypericum perforatum, Ilex paraguariensis, Illicium verum, Jasminum grandiflorum, Juniperus communis, Kigelia africana, Lagerstroemia indica, Lamium album, Larrea tridentata, Lavanda multifida, Lavanda penduculata, Lavanda pinnata, Lavanda stoechas, Lavanda viridis, Lavandula angustifolia, Lavandula latifolia, Leontopodium alpinum, Leptospermum scoparium, Limnanthes alba, Linum usitatissimum, Litchi sinensis, Lithospermum erythrorhizon, Lonicera sp., Luffa cylindrica, Malva sylvestris, Mangifera indica, Matricaria chamomilla, Medicago sativa, Melaleuca altemifolia, Melissa officinalis, Morinda citrifolia, Morus bombycis, Morus nigra, Nardostachys jatamansi, Nasturtium officinale, Oenothera biennis, Olea europaea, Oryza sativa, Padina pavonica, Paeonia albiflora, Paeonia suffruticosa, Palmaria palmata, Panax ginseng, Panicum miliaceum, Papaver somniferum, Passiflora incamata, Paullinia cupana, Pelargonium graveolens, Perilla frutescens, Perilla ocymoides, Persea gratissima, Persicaria hydropiper, Petroselinium crispum, Phyllanthus emblica, Picea abies, Pilocarpus jaborandi, Pinus lambertiana, Pinus sylvestris, Piper nigrum, Pistacia vera, Pisum sativum, Pogostemon cablin, Polygonum cuspidatum, Portulaca oleracea, Prunella vulgaris, Prunus americana, Prunus amygdalus, Prunus armeniaca, Prunus domestica, Pueraria lobata, Punica granatum, Pyrus cydonia, Pyrus malus, Quercus infectoria, Ricinus communis, Robinia pseudoacacia, Rosa canina, Rosa centifolia, Rosa damascena, Rosa mosqueta, Rosa roxburghii, Rosa rubiginosa, Rosmarinus officinalis, Rubia sp., Rubus idaeus, Rubus occidentalis, Rubus ursinus, Ruscus aculeatus, Salix alba, Salix nigra, Salvia officinalis, Sambucus canadenses, Sambucus cerulea, Sambucus nigra, Sapindus mukurossi, Saponaria officinalis, Sargassum filipendula, Saxifraga sarmentosa, Saxifraga stolonifera,*

*Schinus* sp., *Scutellaria baicalensis*, *Serenoa repens*, *Solanum tuberosum*, *Solanum ycopersicum*, *Stryphnodendron* sp., *Symphytum officinale*, *Syzygium aromaticum*, *Tanacetum parthenium*, *Taraxacum officinale*, *Terminalia catappa*, *Terminalia sericea*, *Theobroma cacao*, *Thymus serpyllum*, *Thymus vulgaris*, *Tilia cordata*, *Trifolium pratense*, *Triticum aestivum*, *Tussilago farfara*, *Ulmus rubra*, *Uncaria tomentosa*, *Urtica dioica*, *Vaccinium macrocarpon*, *Vaccinium myrtillus*, *Valeriana officinalis*, *Vanilla planifolia*, *Viola tricolor*, *Vitis* sp., *Ximenia americana*, *Zanthoxylum piperitum*, *Zanthoxylum simulans*, *Zingiber officinale*, *Zingiber zerumbet*, *Ziziphus jujuba* and a mixture thereof.

3. The formulation according to claim 1, wherein the plant extract is hydroglycolic extract or glycolic extract.

4. The formulation according to claim 1, wherein the plant extract is an extract of *Calendula arvensis*, *Calendula bicolor*, *Calendula eckerleinii*, *Calendula lanzae*, *Calendula maderensis*, *Calendula maritima*, *Calendula maroccana*, *Calendula meuselii*, *Calendula officinalis*, *Calendula persica*, *Calendula stellata*, *Calendula suffruticosa*, *Calendula tripterocarpa* or mixtures thereof.

5. The formulation according to claim 4, wherein the plant extract is an extract of *Calendula officinalis*.

6. The formulation according to claim 1, wherein the formulation has a pH in the range of 6 to 8.

7. The formulation according to claim 1, wherein the biosurfactant is selected from the group consisting of monoramnolipids, dirhamnolipids, sophorolipids, mannosylerythritol lipids, cellobiose, xylolipids, trehalipids, lipopeptides, glycosides, rhamnose, and mixtures thereof.

8. The formulation according to claim 1, wherein the extracting agent is selected from the group consisting of: water, chloroform, ethanol, ethers, methanol, polyethylene glycols, propylene glycols, surfactants and a mixture thereof.

9. The formulation according to claim 8, characterized by the fact that wherein the surfactants are selected from the group consisting of: sulphonic acid, alkanolamides, ethoxylated alcohols and alkylphenols, alkyl polyglycosides, ethoxylated fatty amines, cetyltrimethylammonium bromide, benzalkonium chlorides, cetyltrimethylammonium chloride, cocamidopropyl betaine, coconut fatty acid diethanolamide, fatty acid esters, cyclic anhydrohexitoses esters, ethoxymines, sodium lauryl ether sulfate, ammonium lauryl sarcosinate, sodium lauroyl sarcosinate, ammonium lauryl sulfate, octoxynol, amine oxides, polyoxyethylene, tridecyl and surfactants, carboxymethylates, nonnitrogen cations, phosphates, organosiliconate, polymers, ammonium quatemaries, sulfated, sulphonates or a mixture thereof.

10. The formulation according to claim 1, wherein the one or more pharmaceutically acceptable excipients include at least one antioxidant selected from the group consisting of alpha lipoic acid, ascorbic acid, citric acid, ellagic acid, ferulic acid, retinoic acid, anthocyanins, beta-carotenes, bisulfites, cysteine hydrochloride, quercetin, rutin, kaempferol, myricetin, hyperoside, hydroquinones, butylated hydroxyanisole (BHA), butylated hydroxytoluene (BHT), isothiocyanates, metabisulfites, polyphenols, propylgalates, resveratrol, cellobiose, tyrol, glycosides, thiosorbitol and tocopherols.

11. The formulation according to claim 1, wherein the one or more preservatives is selected from the group consisting of phenylmercury acetate, benzoic acid, boric acid, dehydroacetic acid, formic acid, propionic acid, salicylic acid, sorbic acid, undecylenic acid, benzyl alcohol, ethyl alcohol, phenethyl alcohol, benzyl hemiformal, benzyl paraben, benzisothiazolinone, sodium benzoate, polyaminopropyl biguanide, sodium borate, domiphen bromide, bronidox, bronopol, iodopropynyl butylcarbamate, butylparaben, caprylyl glycol, clofucarban, chloramine-T, benzalkonium chloride, benzethonium chloride, silver chloride, chlorhexidine, chlorphenesin, chloroacetamide, chlorobutanol, chlorocresol, chlorophene, chloroxylenol, phenolic preservatives, sodium dehydroacetate, chlorhexidine diacetate, diazolidinyl urea, chlorhexidine dihydrochloride, chlorhexidine digluconate, dimethyloxazolidine, dioxane diol, hexamidine diisethionate, DMDM hydantoin, 2-bromo-2-nitropropane-1, ethylparaben, sodium ortho-phenylphenol, phenoxyethanol, phenoxypropanol, glutaral, hexetidine, sodium hydroxymethylglycinate, hinokitiol, imidazolidinyl urea, sodium iodide, isobutylparaben, isopropylparaben, isothiazolinone, methylamine, methyldibromo glutaronitrile, methylparaben, nisin, nitronersol, o-cymen-5-ol, o-phenylphenol, p-Chloro-m-cresol, propylparaben, calcium propionate, sodium propionate, quaternium 15, quaternium 73, resorcinol, 7-ethylbicycloxazolidine, potassium sorbate, thimerosal, thymol and a mixture thereof.

12. The formulation according to claim 1 wherein the one or more pharmaceutically acceptable excipients selected from antioxidants and precipitants includes at least one precipitant selected from the group consisting of acetic acid, polyacrylic acid, sulfosalicylic acid, trichloroacetic acid (TCA), sodium bicarbonate, carboxymethylcellulose (CMC), diethyl ether, chitosan, neutral salts, ammonium sulphate, methyl tert-butyl ether and a mixture thereof.

13. The formulation according to claim 1, wherein the formulation comprises
2 to 6% of said medicinal plant, part or extract thereof;
0.1 to 5% of biosurfactant;
8 to 62.2% of one or more extracting agents;
0.15 to 6.5% of antioxidant;
0.03 to 0.32% of preservative;
2 to 8% precipitant; and
solvent q.s.p.,
wherein the pH of the formulation can be adjusted with a pH modifier which is an acidulant or an alkalinizer; and
wherein the formulation is for treatment of an injury selected from one or more members of the group consisting of pressure injuries, venous ulcers, diabetic foot ulcers, cuts in skin, scratches, rashes, burns and radiodermatitis to accelerate regeneration of at least one of skin and a dermal mucous membrane.

14. The formulation according to claim 13, wherein the formulation comprises
2 to 6% of powder of *Calendula officinalis* flower;
0.1 to 5% of a mixture of mono-rhamnolipids and dirhamnolipids;
5 to 35% of ethyl alcohol from cereals;
2 to 12% of polyethylene glycol 400;
0.2 to 4% of coconut fatty acid diethanolamide;
0.4 to 3% of cocamidopropyl betaine;
0.1 to 1.2% of sodium lauroyl sarcosinate;
0.2 to 2.0% of octoxynol;
0.1 to 5.0% of sodium lauryl ether sulfate;
0.05 to 2.5% of quercetin;
0.1 to 4.0% of ascorbic acid;
0.2 to 0.27% of methylparaben;
0.01 to 0.05% of propylparaben;
2.0 to 8.0% of sodium bicarbonate; and
purified water q.s.p.,
wherein the pH of the formulation is adjusted with a pH modifier which is an acidulant or an alkalinizer.

15. The formulation according to claim 14, wherein the pH modifier is an acidulant or an alkalinizer, wherein the acidulant is selected from the group consisting of acetic acid, citric acid, ascorbic acid, adipic acid, phosphoric acid, glyoxylic acid, fumaric acid, lactic acid, lactobionic acid, malic acid, propionic acid, sorbic acid, succinic acid, tartaric acid, glucono-delta-lactone (GDL) and a mixture thereof; and the alkalinizer is selected from the group consisting of aminomethyl propanol, sodium bicarbonate, sodium borate, potassium citrate, sodium hydroxide, aluminum hydroxide, triethanolamine and a mixture thereof.

16. The formulation, as defined in any of claim 1, wherein the formulation is an Active Pharmaceutical Ingredient (API).

17. A method for treating an injury comprising:
Applying to the injury a topical pharmaceutical formulation, the formulation including:
  at least one medicinal plant, part or extract thereof which is a source of triterpenoid monoesters;
  two or more extracting agents, wherein at least one extracting agent is a biosurfactant;
  one or more pharmaceutically acceptable excipients selected from antioxidants and precipitants;
  one or more preservatives;
preserving a pH of the topical pharmaceutical formulation in the range of 4.5 to 10 with one or more pH modulators.

18. The method of claim 17 further comprising:
Accelerating a tissue regeneration process of the skin, dermal mucous membrane, to act in protection, maintenance and balance of natural regeneration of at least one of the skin, dermal mucous membrane and related parts.

19. The method of claim 17 further wherein said applying is to at least one injury selected from the group consisting of Use, according to claim pressure injuries, venous ulcers, diabetic foot ulcers, cuts in skin, rashes and burns, and radiodermatitis.

20. The method of claim 17 wherein said applying includes topical use after one of sun lotion, baby rash gel and healing liquid for spray application.

* * * * *